US00PP16157P3

(12) United States Plant Patent
Coiner

(10) Patent No.: US PP16,157 P3
(45) Date of Patent: Dec. 13, 2005

(54) HYBRID TEA ROSE PLANT NAMED 'MISS AMBER'

(50) Latin Name: *Rosa hybrida*
Varietal Denomination: Miss Amber

(75) Inventor: James W Coiner, La Verne, CA (US)

(73) Assignee: Coiner Nursery, LaVerne, CA (US)

( * ) Notice: Subject to any disclaimer, the term of this patent is extended or adjusted under 35 U.S.C. 154(b) by 0 days.

(21) Appl. No.: 10/015,905

(22) Filed: Dec. 5, 2001

(65) Prior Publication Data

US 2003/0106118 P1 Jun. 5, 2003

(51) Int. Cl.[7] ..... A01H 5/00

(52) U.S. Cl. ..... Plt./136

(58) Field of Search ..... Plt./130, 135, Plt./ 136, 137, 139

*Primary Examiner*—Howard J. Locker
(74) *Attorney, Agent, or Firm*—Christie, Parker & Hale, LLP

(57) ABSTRACT

A new and distinct Hybrid Tea Rose plant variety with orange-red flowers.

1 Drawing Sheet

Classification: The present invention relates to a new *Rosa hybrida* plant.

Variety denomination: The new plant has the varietal denomination 'Miss Amber'.

BACKGROUND OF THE INVENTION

The present invention relates to a new and distinct variety of rose plant of the hybrid tea rose of the genus *Rosaceae* which was created by crossing as seed and pollen parents two (2) unknown rose varieties. The varietal denomination of the new variety is 'Miss Amber'.

SUMMARY OF THE INVENTION

Among the novel characteristics possessed by this new variety which distinguishes it from other varieties of which I am aware, is its orange-red flowers.

Asexual reproduction by propagation by budding of the new variety onto 'Dr. Huey' rootstock as performed in Wasco, Calif. shows that the foregoing and other distinguishing characteristics come true to form and are established and transmitted through succeeding propagations.

BRIEF DESCRIPTION OF ILLUSTRATION

The accompanying illustration shows typical specimens of the flowers and foliage of the new variety depicted in color as nearly true as it is reasonably possible to make the same in a color illustration of this character.

DESCRIPTION OF THE NEW VARIETY

The following is a detailed description of 2-year budded plants of the new variety, with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of specimens grown outdoors in Wasco, Calif., during November budded on 'Dr. Huey' understock.

Plant:

*Form.*—Spreading.

*Growth.*—Semi-vigorous.

*Size.*—Height about 36 inches; width about 36 inches.

*Foliage.*—Size: Terminal leaflet length about 2¼ inches; width about 1½ inches. Quantity: Compound, typically 3 leaflets per leaf. Color: New foliage: Upper side near 178A; under side near 179A. Mature foliage: Upper side near 137A; under side near 137D. Shape: Elliptic. Texture: Upper side: Smooth, semi-glossy. Under side: Matte. Edge: Serrated. Serration: Serrate.

*Petioles.*—Top surface color near 143B; Under side near 143C.

*Stipules.*—Medium length.

*Rachis.*—Few prickles.

Wood:

*New shoots.*—Bark: Smooth. Wood: Near 178B.

*Old wood.*—Bark: Smooth. Wood: Near 143A.

*Flowering stem.*—Length about 12 inches.

*Winter hardiness.*—Completely winter hardy.

*Preferred growing conditions.*—Full sun.

*Growth habit.*—Medium vigor.

*Leaves per stem.*—About 5.

Prickles/thorns: New thorns about 3/16 in., color near 142B; mature thorns about ⅜ in., color near 144B.

Flower/inflorescence:

*Blooming habit.*—Continuous. Bud: Length about 2 inches; width about 1 9/16 inches. Form: Classic rose form. Color: Before sepals divide color near 33A; when sepals first divide color near 33A; when petals begin to unfurl color near 37A.

*Sepals.*—Long and thin, usually about 5 sepals 1 inch long by ¼ inch wide with a few small extensions. Size: Length in relation to bud, about 1½ inches. Color: Topside near 143B; bottom near 144A.

*Peduncle.*—Length: About 3 inches, usually bearing numerous small acicular projections; Strength: Erect. Color: Near 143C, at times slight anthocyanin in coloration; color near 57C.

*Flower.*—Size: About 5¼ inches. Borne: Single. Form: High center; unfurls full.

*Petalage.*—About 26. Petaloids in center: About 7. Persistence: Petals do not drop.

*Fragrance.*—Slight.

*Lasting quality.*—About 3 weeks on plant; about 7 days after cutting.

*Color.*—During first 2 days: Inner petals at flower center topside near 37A; bottom near 38A; outer petals topside near 37B, bottom near 38B.

*Base of petals* (*point of attachment*).—Near 2A.

*General tonality from a distance.*—Near 34B.

*Color change.*—Remains the same even after 3 or more days.

Petals:

*Texture.*—Thin, soft, velvet texture.

*Size.*—About 1½ inch long by about 1¼ inch wide.

*Shape.*—Oval; Length approximately 1⅝ in., width approximately 1¼ in.

*Color.*—Top — near 34A; Bottom — near 35B.

*Margin.*—Slightly serrated.

*Arrangement.*—Imbricated.

*Appearance.*—Velvety.

Reproductive organs:

*Arrangement of stamens, filaments and anthers.*—Regularly arranged around styles.

*Color.*—Filaments near 7A; Anthers near 10A.

*Pollen.*—No pollen.

*Styles.*—Thin; medium length, about 110 anthers and filaments.

*Stigma.*—Color: Near 16D.

*Hips/seed vessels/ovaries.*—Shape: Round. Size: Small; about ¼ inch. Color: Near 138B. Seeds: No seeds.

Disease resistance: The cultivar has average disease resistance/ susceptibility.

I claim:

1. A new and distinct Hybrid Tea Rose plant of the variety substantially as shown and described.

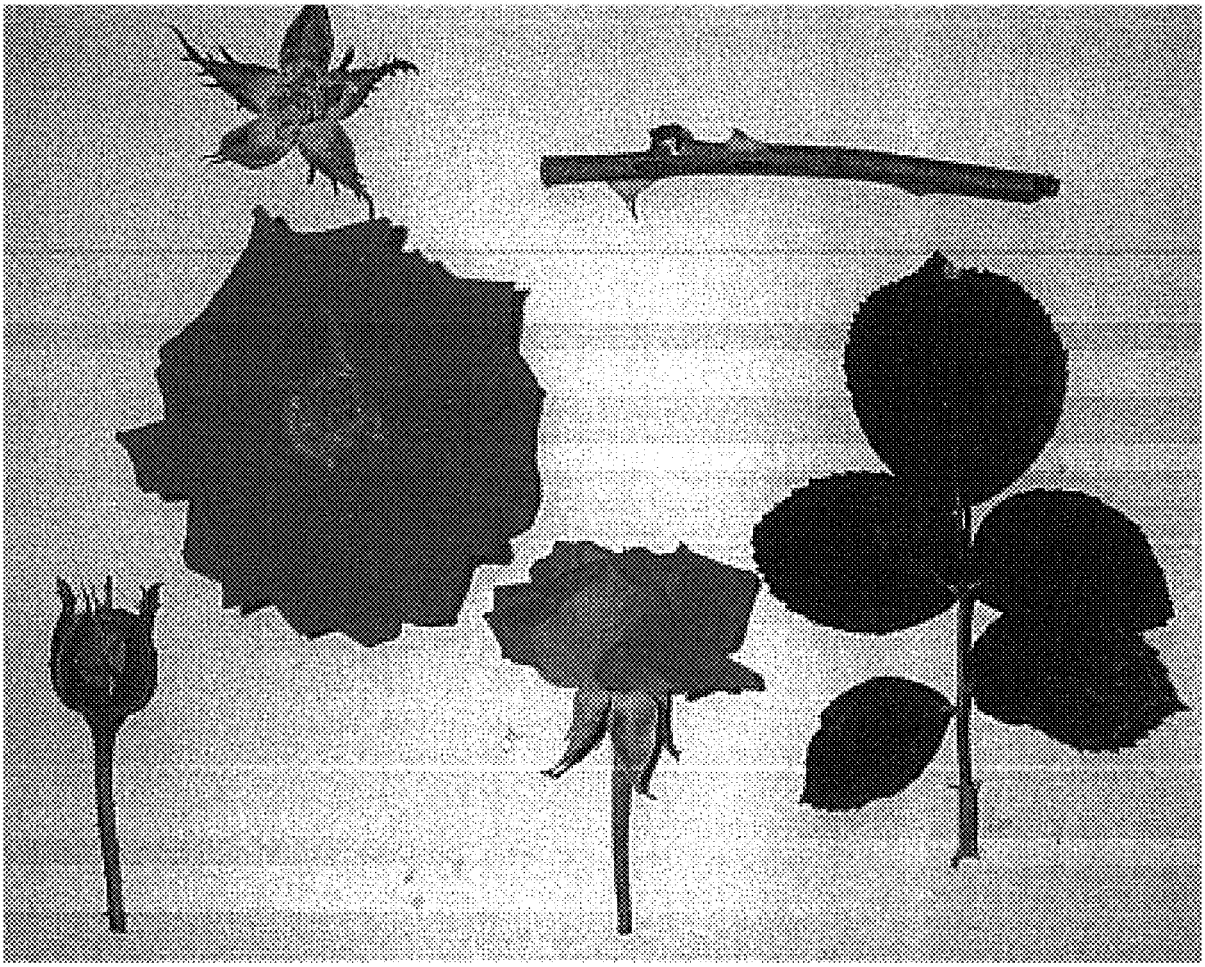

* * * * *